United States Patent
Fischer et al.

(10) Patent No.: US 10,682,159 B2
(45) Date of Patent: *Jun. 16, 2020

(54) ABRASIVE BODY

(71) Applicant: Lukas-Erzett Vereinigte Schleif-und Fraswerkzeugfabriken GmbH & Co. KG, Engelskirchen (DE)

(72) Inventors: Gerd Fischer, Gummersbach (DE); Bernhard Runden, Bornheim (DE)

(73) Assignee: Lukas-Erzett Vereinigte Schlief- und Fraswerkzeugfabriken GmbH & Co KG, Engelskirchen (DE)

( * ) Notice: Subject to any disclaimer, the term of this patent is extended or adjusted under 35 U.S.C. 154(b) by 213 days.

This patent is subject to a terminal disclaimer.

(21) Appl. No.: 15/903,953

(22) Filed: Feb. 23, 2018

(65) Prior Publication Data

US 2018/0177529 A1     Jun. 28, 2018

Related U.S. Application Data

(62) Division of application No. 14/783,899, filed as application No. PCT/EP2014/057418 on Apr. 11, 2014, now Pat. No. 9,924,967.

(30) Foreign Application Priority Data

Apr. 11, 2013  (DE) .................. 10 2013 103 643

(51) Int. Cl.
*A61B 17/54* (2006.01)
*B24D 3/34* (2006.01)
(Continued)

(52) U.S. Cl.
CPC .............. *A61B 17/54* (2013.01); *A45D 29/04* (2013.01); *A61C 3/06* (2013.01); *B24D 3/346* (2013.01);
(Continued)

(58) Field of Classification Search
CPC ........ A61B 17/54; A61B 2017/320004; B24D 11/00; B24D 3/346; B24D 7/00; A45D 29/04; A45D 2029/045; A61C 3/06

See application file for complete search history.

(56) References Cited

U.S. PATENT DOCUMENTS 4,829,539 A * 5/1989 Angus .................... G01K 11/06
374/159
4,954,140 A * 9/1990 Kawashima ............. B24D 3/28
51/293

(Continued)

FOREIGN PATENT DOCUMENTS

CN          1886232 A     12/2006
CN        101238178 A      8/2008
(Continued)

OTHER PUBLICATIONS

International Search Report dated Jul. 15, 2014, International Application PCT/EP2014/057418, dated Apr. 11, 2014.

*Primary Examiner* — Julian W Woo
(74) *Attorney, Agent, or Firm* — Dinsmore & Shohl LLP

(57) ABSTRACT

The invention relates to an abrasive body (6) for a grinding tool with an abrasive layer (8), which has at least one binding agent (12) and abrasive grains (13), characterised in that thermochromic colouring agents are provided in the abrasive layer (8).

The invention relates further to a grinding tool (1) with an abrasive body (6) according to the invention and elements (5) for connecting the grinding tool (1) to a driving device for rotatingly driving the abrasive body (6).

The invention relates further to a use of the abrasive body (6) according to the invention or of the grinding tool (1) according to the invention for treating human body parts.

20 Claims, 2 Drawing Sheets

(51) Int. Cl.
    *A45D 29/04*     (2006.01)
    *A61C 3/06*     (2006.01)
    *B24D 7/00*     (2006.01)
    *B24D 11/00*     (2006.01)
    *A61B 17/32*     (2006.01)

(52) U.S. Cl.
    CPC ............... *B24D 7/00* (2013.01); *B24D 11/00* (2013.01); *A45D 2029/045* (2013.01); *A61B 2017/320004* (2013.01)

(56) References Cited

U.S. PATENT DOCUMENTS

| | | | | |
|---|---|---|---|---|
| 5,611,829 | A * | 3/1997 | Monroe | C04B 35/1115 501/128 |
| 5,908,477 | A * | 6/1999 | Harmer | B24D 3/004 451/59 |
| 6,027,402 | A * | 2/2000 | Oliver | A45D 29/04 132/76.4 |
| 6,145,512 | A | 11/2000 | Daley | |
| 7,304,008 | B2 * | 12/2007 | Belykh | C03C 8/00 374/E11.02 |
| 7,364,789 | B2 * | 4/2008 | Eguchi | B24D 3/32 428/323 |
| 8,449,635 | B2 * | 5/2013 | You | B24D 3/34 430/270.1 |
| 8,911,861 | B2 * | 12/2014 | Parker | G01K 11/165 252/586 |
| 9,924,967 | B2 * | 3/2018 | Fischer | A45D 29/04 |
| 2004/0014396 | A1 | 1/2004 | Elledge | |
| 2005/0113005 | A1 | 5/2005 | Woo et al. | |
| 2006/0242910 | A1 | 11/2006 | You | |
| 2007/0221238 | A1 | 9/2007 | Tran et al. | |
| 2010/0227531 | A1 | 9/2010 | Wijaya | |
| 2014/0318025 | A1 | 10/2014 | Gaeta et al. | |

FOREIGN PATENT DOCUMENTS

| | | |
|---|---|---|
| DE | 202007012818 U1 | 11/2007 |
| DE | 202009006069 U1 | 8/2009 |
| EP | 2578180 A1 | 4/2013 |

* cited by examiner

ABRASIVE BODY

CROSS-REFERENCE TO RELATED APPLICATIONS

This Application is a Divisional Application of U.S. application Ser. No. 14/783,899 filed Oct. 12, 2015 now U.S. Pat. No. 9,924,967. Application Ser. No. 14/783,899 claims the benefit of U.S. national stage application PCT/EP2014/057418 filed Apr. 11, 2014, which claims priority of German Patent Application 10 2013 103 643.0 filed Apr. 11, 2013, the contents of which are incorporated herein in their entirety.

FIELD OF THE INVENTION

The present invention relates to an abrasive body for a grinding tool with an abrasive layer, which has at least one binding agent and abrasive grains. Furthermore, the present invention relates to a grinding tool with such an abrasive body. Furthermore, the present invention relates to a use of such an abrasive body or such a grinding tool.

BACKGROUND OF THE INVENTION

Abrasive bodies and grinding tools of this type are known and are for example used for processing metal or wood, for manufacturing prostheses or for the podiatry or manicure. As during grinding processes temporarily and locally a high heat loading can be produced, it is repeatedly necessary, to interrupt the grinding process, to cool the abrasive body and the to be processed areas. Furthermore, it is known, to cool the abrasive body during the grinding process, to prevent pain caused by heat in the patient or to prevent heat damages on the to be worked workpiece.

A grinding tool of the above mentioned type is for example described in DE 20 2007 012 818 U1. The grinding tool known from this printed document, is used in the field of podiatry and has a cap-like abrasive body. The abrasive body consists of a metal substrate layer, on which an abrasive layer is applied. Furthermore, a driving device for the rotational driving of the abrasive cap belongs to the grinding tool, wherein the driving device and the abrasive cap are connected to each other via a clamping shaft. To cool the abrasive body during the grinding process, cooling bores are provided in the abrasive body, via which cooling air flows to the to be treated area from the inside.

It is seen to be a disadvantage, that the cooling, especially during longer treatments, cannot completely discharge the grinding heat, so that local heat damages can be produced. To prevent this, a podiatrist is instructed by a patient when the heat makes the treatment unpleasant. However, the risk of causing burns exists during the treatment, that is especially high with diabetics, whose temperature sensation at the feet is often poor.

From DE 20 2009 006 069 U1 a polishing disc is known that is made from polyurethane foam. The soft polishing disc has thermochromic colouring agents, to indicate optically to a user by means of colour change that the polishing disc is getting hot and consequently can damage the paintwork. The thermochromic colouring agents are enclosed in micro-capsules, which during the manufacture of the polishing disc are added to the flexible foam. The micro-capsules further contain a thermoset resin melting at low temperature and an activator bond. To be able to visually see during the polishing process temperature increases which are damaging the paint work, the thermochromic colouring agent changes its colour at a defined colour change temperature. The thermoset resin, melting at a low temperature, has in the area of this colour change temperature its melting range, so that by means of the melting of the resin, the thermochromic colouring agent reacts with the activator bond.

It is seen to be disadvantageous, that the thermoset resin has to initially melt, before the thermochromic colouring agent changes colour. Furthermore, the manufacture of the polishing disc is cumbersome, as the thermochromic colouring agents have to be enclosed together with the activator bond and the thermoset resin in micro-capsules, to mix these followingly to the flexible foam. Furthermore, it is disadvantageous, that with the soft foam no chipping or cutting processing steps can be carried out on the surfaces of the to be processed materials.

SUMMARY OF THE INVENTION

Against from this state-of-the-art, it is an object of the present invention to provide an abrasive body or a grinding tool, with which the damages caused by heat or pain at the to be treated points can be prevented during a grinding process. Furthermore, it is an object of the present invention, to provide an abrasive body or grinding tool, by means of which prevents damage caused by heat and pain to the treated human patient.

To this object, the present invention provides an abrasive body of the above mentioned type, in which thermochromic colouring agents are provided in the abrasive layer.

According to the invention the effect of the thermochromism is used, according to which specific substances change their colour during heating or cooling. In this manner a user of the abrasive body, for example a podiatrist or a mechanic can determine, how hot the outer face of the abrasive body is. Thus, the user can, at an early stage, interrupt the grinding process, to prevent an excessive heating of the to be treated area. Thus, the abrasive body according to the invention is especially suitable for the treatment of patients, for example in the field of podiatry, manicure or in the dental field. Furthermore, the abrasive body can also be used in grinding processes on materials which should be prevented from being subjected to excessive heat by means of the frictional heat produced during the grinding.

In a preferred manner it is provided, that the abrasive body is formed from a plurality of layers and has a substrate layer. The substrate layer can for example be manufactured from a rigid form-stable backing for abrasives made from metal or from other form-stable material. Alternatively, the substrate layer can also be a flexible backing for abrasives made from a textile, especially cotton wool. For example, the substrate layer made from cotton wool can be provided with an impregnation mass, on which the abrasive layer with at least one binding agent can especially be directly applied. In contrast, the abrasive body can also manage without a substrate layer. This is especially then the case, when the abrasive body is formed as elongated grinding pin or disc-like grinding stone.

Advantageously, the thermochromic colouring agents comprise an amount of thermochromic colour pigments with the same characteristics or at least a mixture of diverse thermochromic colour pigments. Alternatively or additionally, the thermochromic colouring agents comprise a thermochromic colourant or at least a mixture of diverse thermochromic colourants. The thermochromic colourant distinguishes itself from others in that fact, that it is solubly bound in the abrasive layer, especially at least in a binding agent, in contrast to which the thermochromic colour pigments are generally non-soluble and are mixed to the abrasive layer, especially at least to the one binding agent.

Advantageously, it is provided, that the abrasive layer is built up from a plurality of layers and has at least one inner and one outer bonding layer. In other words, the abrasive layer has a multi-layered structure with several bonding layers, wherein the bonding layers have a binding agent. Generally, besides the inner and the outer bonding layer, further central bonding layers can be provided in the abrasive layer, so that also more than the two mentioned bonding layers are possible.

Advantageously, the inner bonding layer is formed as a base layer with the at least one binding agent and the outer bonding layer is formed as a cover layer with a further binding agent. Generally for the base layer and the cover layer also the same binding agent can be used. At the example of a two-layered structure of the abrasive layer, an inner bonding layer, namely the base layer, is applied on the substrate layer. The abrasive grains can be applied onto the base layer, the grains can be scattered electrostatically or mechanically. The at least one binding agent of the base layer holds the abrasive grains in the abrasive layer, to prevent a grain break-out. Then an outer bonding layer, namely the cover layer, is applied over the base layer. Because of the cover layer, the retaining of the abrasive grains in the abrasive layer is improved. Because of the multi-layered structure of the abrasive layer, the danger of a breaking-out of a grain is thus clearly reduced. The final cover layer is not a flat, smooth finishing face of the abrasive layer, but due to the abrasives projecting partially from the layer forms a clefted, uneven abrasive face. With the starting of a grinding process, initially the areas of the cover layer around the abrasive grains is removed on a new abrasive body, whereby the abrasive grains are partially exposed. With advancing use of the abrasive body, constantly larger areas of the cover layer are removed, till the cover layer is completely removed. Because of the multi-layered structure of the abrasive layer, the abrasive grains are held also after depletion of the cover layer at least by the base layer. When the abrasive body has no substrate layer, such as elongated abrasive stones or round abrasive discs, the abrasive body has only the abrasive layer with several bonding layers, in which the abrasive grains are bound.

Furthermore, at least one additional coating layer, for example an anti-adhesion layer can be provided on the cover layer, to prevent the adhesion of grinding dust particles on an outer face of the abrasive body. Thus, during the grinding the clogging of the abrasive body is reduced. In this case, the anti-adhesion layer can not only be provided as the outmost layer on the abrasive body, but can also be integrated in one of the bonding layers of the abrasive body.

According to an aspect of the present invention it is provided, that the inner bonding layer is free of thermochromic colouring agents. Especially, the thermochromic colouring agents are only provided in the cover layer. Thus, the user can determine during the application of the abrasive body not only its outer face temperature, but determine by means of the wear of the at least at predetermined temperature ranges coloured cover layer, the degree of wear of the abrasive body. Furthermore, the cover layer can also be applied with the thermochromic colouring agents later on an abrasive body, to provide the customery abrasive bodies with thermochromic colouring agents. Furthermore, the cover layer may also have further bonding layers, especially central bonding layers between the base layer and the cover layer, can have thermochromic colouring agents, to be able to see, in steps, the wear of the individual bonding layers.

To be able to observe the thermochromic colouring agents better from the outside, the binding agent of the cover layer can be a transparent binding agent. Furthermore the taken-up colour of the thermochromic colouring agents is not falsified by the binding agent and layers arranged below the cover layer are better distinguishable due to their own colour provided. Especially good results were achieved such, that the binding agent of the cover layer is a transparent thermosetting plastic or a transparent thermosetting binding agent. Thus, a more or less transparent and colourless resin is used in the cover layer or a central bonding layer and fillers, except possibly added thermochromic colouring agents and/or abrasive grains can be as far as possible omitted. Preferably, the amount of resin in the cover layer minus the abrasive grains after the hardening, is larger than 70 percent, especially larger than 90 percent, and in a preferred manner larger than 95 percent. When the at least essentially transparent, translucent or less opaque cover layer wears, its covering force is reduced continuously. Thus, between the thermochromic colouring agents of the cover layer and a layer, dyed and arranged below, mixed colours are produced, so that the user of the abrasive body can observe the amount of wear of the abrasive layer until the cover layer is completely depleted.

In preferred manner the binding agent of the base layer can be an organic or an inorganic binding agent. For example, it can be a resin, which in the temperature range occurring during the grinding process does not melt, or can be a ceramic binding agent. In ceramic bound grinding means, the inorganic binding agent of the base layer can for example be ceramic or glass between the abrasive grains. The cover layer is then applied in a second step after the firing of the inorganic binding agent.

According to an aspect of the present invention, non-thermochromic colours are provided in the base layer. This, however, does not exclude, that in the base layer also thermochromic colouring agents can be provided. For example, the non-thermochromics colouring agents can have a red colour of its own. Thus, diverse changes of colour can be achieved, wherein in this case a possible change of colour is exemplary explained: The thermochromic colouring agents are for example only provided in the cover layer and have a mixture of thermochromic colouring agents, which comprise two different groups of thermochromic colour pigments. The first group has blue thermochromic colour pigments, which become transparent at a colour change temperature of 40 degrees Celsius, and the second group has yellow thermochromic colour pigments, which become transparent at a colour change temperature of 60 degrees Celsius. The base layer is, in this case, dyed red with a non-thermochromic colouring agents. Thus, at room temperature a mixed colour is achieved, which turns the abrasive layer green. If the temperature of the abrasive layer increases above 40 degrees Celsius, the abrasive layer turns yellow and is red above 60 degrees Celsius. When the relative amount of pigments of the blue colour pigments is increased in relation to the yellow thermochromic colour pigments, the colour sequence could look like as follows: At room temperature the abrasive layer is blue up to blue/green. Around 40 degrees Celsius the colour of the abrasive layer turns from green to green/yellow and above 60 degrees Celsius it turns red. Beside being able to determine the temperature of the abrasive layer, the wear of the cover layer can be better observed by the dyed base layer. During the operation of the abrasive body, the cover layer is locally removed, till it is depleted. The abrasive grains are worn with time and/or are blunted, so that the used abrasive body produces because of the larger abrasive surface more frictional heat than a new abrasive body. When the cover layer is depleted or is completely used, the risk of a breaking-out of a grain of the abrasive grains from the base layer increases. Because of its own colour of the base layer, thus, the degree of wear of the abrasive layer provided with thermochromic colouring agents, especially of the cover layer become visible from the outside.

Furthermore, on an upper face of the substrate layer, facing to the abrasive surface, a non-thermochromic colour can be applied. Thus is provided a further manner for determining the degree of wear of the abrasive body, which is very visible in a transparent base layer.

In a preferred manner, a partial amount of the abrasive grains are formed transparent. Preferably, all abrasive grains can be transparent. Transparent abrasive grains made from monocyrstalline aluminium oxide are suitable. Because of the transparent structure of the abrasive grains, the thermochromic colouring agents and the possibly provided non-thermochromic colouring agents are easier to determine and their colours are not altered by the colour of the abrasive grains.

Additionally or alternatively to the transparent abrasive grains, at least a partial amount of the abrasive grains can be coloured. Especially all abrasive grains can be coloured. Depending on the grinding task, different abrasive grains can be advantageous. Not only or instead of the transparent monocyrstalline aluminium oxide, red fused aluminium, green silicon carbide or white abrasive grains, such as ceramic grains, Sol-gel corundum or fused aluminium in white can be used. When using coloured abrasive grains, the colour of the base layer can be adapted by mixing the binding agent of the base layer with non-thermochromic colourants to the colouring agents of the abrasive grains.

To be able to achieve especially good grinding results with the abrasive body, the abrasive grains can have a grain size between 30 and 1400 micrometers. Because of the large grain sizes, the chipping space between the abrasive grains is large enough, that the abrasive body is not clogged, for example, during the removal of callused skin on human feet. If the chipping space is however too small, the chipping volume or the cutting capacity of the abrasive body is reduced and the danger increased, that the abrasive body and the patient or the to be treated component is damaged by a quickly increasing outer face temperature of the abrasive body.

In a preferred manner, the thermochromic colouring agents comprise reversible and/or non-reversible thermochromic colouring agents. With the example of a thermochromic colouring agent which in the cooled condition, for example at room temperature, is dark-coloured, a temperature increase can be signalled to the user by means of change of the colour. The initially dark thermochromic colouring agent can for example indicate the temperature increase with a colour change to red. Thus, the user can determine in a simple manner the outer face temperature of the abrasive body. If for example reversible colouring agents are used, not only the heating of the abrasive body is indicated to the user by means of the colour change, but also its cooling, as the abrasive body turns to its original colour in the cooled condition. If additionally or alternatively irreversible colouring agents are used, it can be indicated permanently to the user, that the abrasive body was operated above a maximum allowed outer face temperature. Thus, the irreversible color agent permanently shows that the abrasive body was overheated and is not suitable anymore for the further use. As long as the abrasive body is operated below the predetermined maximal temperature, the abrasive body returns in the cooled condition to its original colour. If only irreversible colouring agents are used, the agents will turn in colour when reaching a predetermined outer face temperature. Thus, it can permanently be shown, that the abrasive body has already been used once. This ensures, that only new abrasive bodies with an impeccable abrasive layer are used. This is ensured in the simplest manner, when the colour change temperature is just above the room temperature.

Advantageously, the thermochromic colour pigments are formed such, that their colour changes at least once at an outer face temperature between 20° Celsius and 90° Celsius. Depending on the required grinding application, the thermochromic colour pigments can however also be formed such, that their colour already changes once at an outer face temperature between 30° Celsius and 70° Celsius. In general, the selection of the colour pigments is based on the intended grinding application of the abrasive body. Starting from the interesting thermosensitive range of patients or of the workpiece, then such thermochromic colour pigments are selected, based on which colour changes at least once in the temperature range or when reaching the maximum allowed grinding temperature. As the abrasive body heats up from the outside inwards, during the grinding process also at the same grinding application thermochromic colour pigments or thermochromic colourants of different colour change temperatures can be used. Depending on where the thermochromic colouring agents are provided, thus, the at least one colour change temperature of thermochromic colouring agents on the outside has to be correspondingly lower than that of the inwardly arranged colouring agents.

In a preferred manner the thermochromic colouring agents are formed such, that their colour changes at least once at an outer face temperature between 40° Celsius and 60° Celsius. This range is especially good for the podiatry.

Especially advantageously, the thermochromic colouring agents have several defined colour change temperatures. By means of fine scaled colour changes, the user can exactly determine the outer face temperature of the abrasive body. By means of mixing diverse thermochromic colour pigments and/or thermochromic colourants, diverse reversible and/or irreversible colour sequences with different colour change temperatures can be achieved.

Furthermore, the thermochromic colouring agents can be formed such, that the at least one colour change of the thermochromic colouring agents is carried out continuously or discontinuously. Advantageously, the thermochromic colouring agents are formed such that the at least one colour change of the thermochromic colouring agents takes place continuously. In this manner, the user can see well the increasing temperature of the abrasive body and can carry out suitable counter measures for cooling the abrasive body, for example removing the abrasive body from the to be treated surface. Alternatively the at least one colour change of the thermochromic colouring agents can take place discontinuously. In a mixture of different thermochromic colouring agents continuous and discontinuously colour changes can be provided. Furthermore, also thermochromic colourants can be provided, which at a first colour change temperature change their colour continuously and at a second colour change temperature change their colour discontinuously.

Advantageously, the thermochromic colouring agents are formed such, that these turn transparent during at least one colour change temperature. In this manner the lower layers become visible when reaching the colour change temperature, so that for example a dyed inner bonding layer or a colour coating on the substrate layer becomes visible from the outside. In a preferred manner the thermochromic colouring agents in the cover layer are formed such, that they turn opaque at least at an outer face temperature of below 20° Celsius and at least at a predefined outer face temperature higher than 20° Celsius turn transparent. Advantageously, an inner bonding layer arranged below the cover layer or the substrate layer is dyed in a warning colour. Thus, for example the thermochromic colouring agents carry out with increasing outer face temperature a predefined colour sequence and at a predefined outer face temperature higher than 20° C. turn transparent. Thus, at the start, a dark coloured layer can turn transparent during the heating of the outer face of the abrasive body and the dyed layer arranged below the cover layer can shine through. For improved visibility, a layer can be dyed in a warning colour, for example in red, yellow or a striking neon colour. Furthermore, a colour can be selected, which corresponds to the colour of the excessive wear for a particular application. Thus, the abrasive body has the same colour when completely covered with wear as well as at increased temperatures. Then, the user realises that he has to interrupt the work. When the abrasive body is clogged with chippings, the colour does not change anymore and the user can see, that he cannot use the abrasive body any further until the colour changes again, so that it is indicated, that the abrasive body is again normally tempered. The cover layer can also be formed such, that it is at least at an outer face temperature of less than 20° Celsius transparent and at least at one defined outer face temperature higher than 20° Celsius opaque. Therefore, a colour which initially shines through the cover layer, can be covered by the cover layer, to indicate in this manner the temperature increase.

Furthermore, the thermochromic colouring agents can be formed such, that a colour change takes place at a first colour change temperature and a further colour change takes place at the second colour change temperature. Advantageously, the colour change at the first colour change temperature is reversible and the colour change at the second colour change temperature is irreversible. In a preferred manner, the second colour change temperature is higher than the first colour change temperature. Thus, the first colour change can, for example, be reversible in a temperature range which is free of risks for a to be treated material or for the patient, so that the abrasive body turns again to its original colour when cooling. If in contrast thereto, the abrasive body is heated beyond a defined temperature, which is for example detrimental for the material or the patient, which leads to burns or which makes the abrasive body useless, the second colour change temperature can be irreversible. The second colour change temperature can also be arranged just above the room temperature, so that the user knows straight away, that the abrasive body has already been used. In this case, the first colour change temperature is arranged in the range of the room temperature, so that the colour of the abrasive body does not already change irreversibly before being used.

In a preferred manner it is provided, that the abrasive body is formed as a rotationally symmetrical abrasive head and is connectable to a drive shaft for the rotational driving. For example, the abrasive body can be manufactured as an abrasive cap with a substrate layer from a flexible material, for example from cotton wool. The abrasive body can also be formed as an abrasive disc.

A further object of the present invention is a grinding tool with the above described abrasive body. The grinding tool has elements for connecting the abrasive body to a driving device for rotatingly driving the abrasive body.

Furthermore, a further object of the present invention is the use of the above described abrasive body or of the above described grinding tool for treating human body parts. In a preferred manner, the abrasive body or the grinding tool are used for the foot care, i.e. in the frame of podiatry.

BRIEF DESCRIPTION OF THE DRAWINGS

A preferred embodiment is described in the following using the figures. It shows.

DETAILED DESCRIPTION OF THE INVENTION

Figure 1:
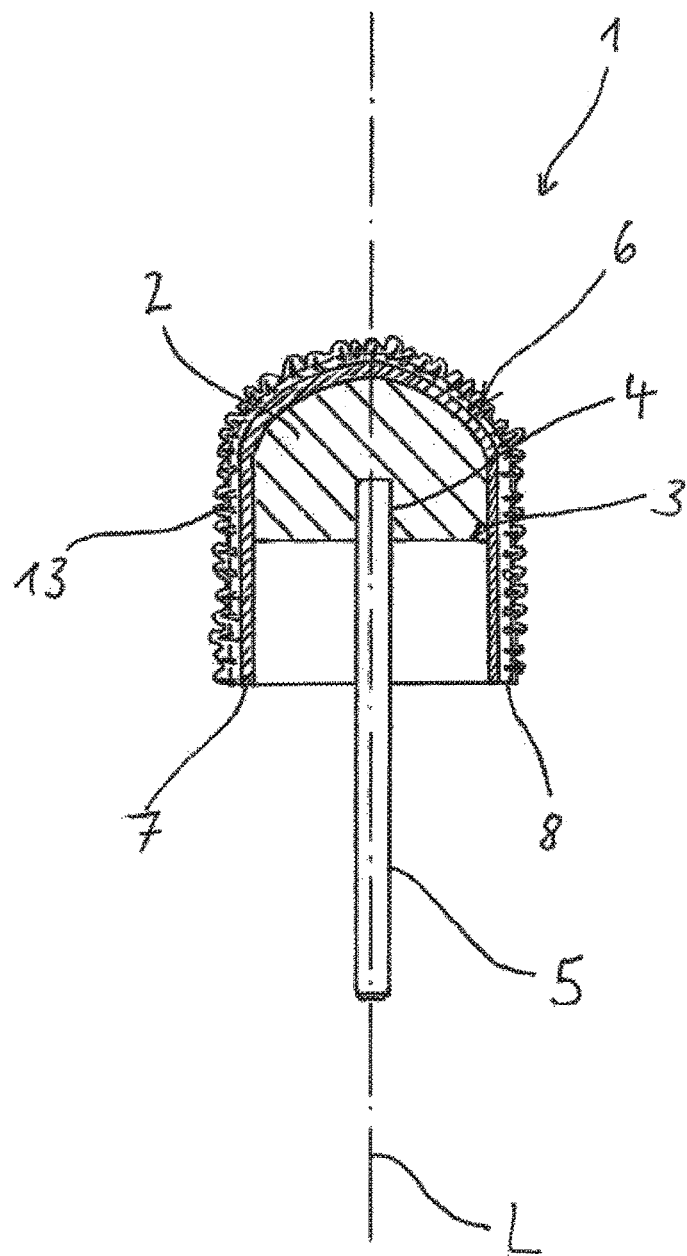
FIG. 1 a longitudinal sectional view of an embodiment of a grinding tool according to the invention.

Shown in FIG. 1 is an embodiment of a grinding tool according to the invention for podiatry, with which especially hardened skin areas of feet can be ground.

The grinding tool comprises a rotationally symmetrical abrasive head 1, which has a core 2, cast from resin. The core is formed hemispherically and has a central bore 4 at a flattened end 3. An elongated shaft 5 is pressed into the bore 4. The shaft 5 is preferably manufactured from metal. Furthermore, a driving device, not shown, is provided, to rotationally drive the abrasive head 1 around its longitudinal axis L. An abrasive cap 6 is glued onto the core, such that the cap 6 protrudes over the core 2 at a flattened end 3 in a longitudinal direction.

Figure 2:
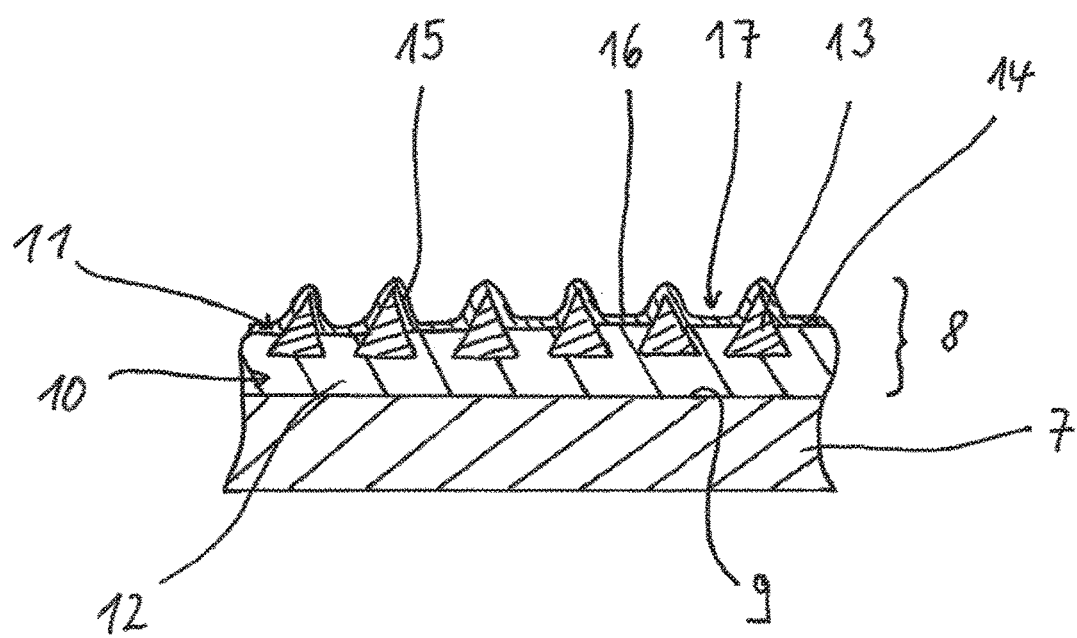
FIG. 2 a longitudinal sectional view of a partial view of an abrasive body according to the invention.

In FIG. 2 a longitudinal sectional view of the abrasive cap 6 according to the invention is shown. It can be seen that the abrasive cap 6 is formed from multiple layers and has a substrate layer 7 and an abrasive layer 8. The substrate layer 7 is made from a flexible cotton fabric and is glued to the core 2, not shown in FIG. 2. On an upper face 9 of the substrate layer 7, facing away from the core 2, the abrasive layer 8 is applied.

The abrasive layer 8 is formed from several layers and has an inner and an outer bonding layer, namely a base layer 10 and a cover layer 11. The base layer 10 is applied on the upper face 9 of the substrate layer 7. This has a ceramic binding agent 12, which is dyed in a red non-thermochromic colour. In the ceramic binding agent 12 of the base layer 10, abrasive grains 13 are embedded. The abrasive grains 13 are transparent monocrystalline aluminium oxides, which are preferably electrostatically scattered in the base layer 10. These have a grain size of approximately 425 micrometers. The base layer 10 and the partially projecting abrasive grains 13 form an uneven, clefted surface 14. On this clefted surface 14, the cover layer 11 is applied, which encases the base layer 10 and the abrasive grains 13 in a relatively thin layer and additionally binds the abrasive grains 13. The cover layer 11 has a transparent thermosetting binding agent 15, which is thermally hardened. Corresponding to the clefted surface 14, the cover layer 11 has an uneven outer face 16. Between the individual abrasive grains 13 spaces 17 are formed, which serve for accommodating separated callus chips during the grinding.

For determining the outer face temperature of the abrasive cap 6, thermochromic colouring agents are bound in the transparent binding agent 15 of the cover layer 11. The thermochromic colouring agents have a mixture of reversible colour pigments, which comprise two evenly distributed groups. The first group has blue thermochromic colour pigments, which turn transparent at a colour change temperature of 40 degrees Celsius, and the second group has yellow thermochromic colour pigments, which turn transparent at a colour change temperature of 60 degrees Celsius. Thus, the cover layer 11, provided with the thermochromic colour pigments, appears at room temperature in a green colour tone.

In operation, the podiatrist removes the abrasive head 1 from a sterile packaging and clamps this by means of the shaft 5 into a chuck of the driving device. During the grinding process the podiatrist presses the abrasive head 1 for example against a hardened skin area of the patient's foot.

Because of the friction between the abrasive layer 8 and the foot of the patient, frictional heat is produced, which leads to an increase of the outer face temperature of the abrasive cap 6. The cover layer 11, which in the cold condition at room temperature is still green, turns yellow starting from an outer face temperature of the abrasive cap 6 of 40 degrees Celsius. Thus the podiatrist recognises, that the outer face temperature of the abrasive cap 6 is at a temperature above 40 degrees Celsius, which is pleasant for the patient, but below 60 degrees Celsius.

If the podiatrist does not remove the abrasive body 1, the outer face temperature of the abrasive cap 6 increases further with longer grinding time. If the outer face temperature exceeds 60 degrees Celsius, the cover layer 11 turns transparent and the red base layer 10 becomes visible. Thus, it is signalled to the podiatrist, that the outer face temperature has reached a temperature which is not pleasant to the patient and that the grinding process should be interrupted for cooling the abrasive cap 6.

As soon as the podiatrist removes the abrasive body 1 from the foot, the abrasive cap 6 can cool down. Then, also the spaces 17 for the chips of the abrasive layer 8 are exposed, into which chips of the callus removed by the abrasive layer 8 were transported during the grinding process. The chips fall thus out of the spaces 14 for chips or can be blown out of them.

Furthermore, the thermochromic colour pigments in the cover layer 11 are not only suitable to indicate the outer face temperature of the abrasive layer 8, but also for determining the wear of the abrasive layer 8. Immediately at the start of the first grinding process, the abrasive layer 8 is slowly removed. The podiatrist can determine its wear in such a way, that initially in the area of the transparent abrasive grains 13, the cover layer 11 dyed with the thermochromic colour pigments and the red base layer 10 arranged below becomes visible in some areas. With increasing wear of the abrasive layer 8, increasingly larger areas of the red dyed base layer 10 become visible, as the cover layer 11 is at least locally further removed around the abrasive grains 113 and is with further application completely consumed. In this manner the podiatrist is shown, that the cover layer 11, together with the base layer 10 give the abrasive grains 13 an additional hold, is gradually consumed. To prevent a breaking-out of the abrasive grains 13, the abrasive cap 6 should not be used anymore, when the base layer 10 is mostly exposed.

By means of mixing diverse thermochromic colouring agents into the individual bonding layers 10, 11, different colour sequences can be achieved. Furthermore, also irreversible thermochromic colouring agents can be provided, to permanently indicate to the podiatrist when exceeding a defined outer face temperature of the abrasive cap 6, that this has been used and should not be used anymore because of hygienic reasons.

REFERENCE SIGNS LIST 1 abrasive head
2 core
3 end
4 bore
5 shaft
6 abrasive cap
7 substrate layer
8 abrasive layer
9 upper face
10 base layer
11 cover layer
12 binding agent of the base layer
13 abrasive grains
14 surface
15 binding agent of the cover layer
16 outer face
17 spaces for the chips
L longitudinal axis

The invention claimed is:

1. A grinding tool comprising:
an abrasive body and elements for connecting the grinding tool to a driving device for rotatingly driving the abrasive body, wherein the abrasive body has an abrasive layer formed of a plurality of bonding layers with at least an inner bonding layer, an outer bonding layer and abrasive grains,
wherein said abrasive grains are applied onto the inner bonding layer, and wherein the outer bonding layer covers the abrasive grains and wherein the outer bonding layer is provided with thermochromic colouring agents.

2. The grinding tool according to claim 1, wherein a binding agent of the inner bonding layer is the same binding agent of a outer bonding layer.

3. The grinding tool according to claim 1, wherein a binding agent of the inner bonding layer and a binding agent of the outer bonding layer are different binding agents.

4. A grinding tool comprising:
an abrasive body and elements for connecting the grinding tool to a driving device for rotatingly driving the abrasive body,
wherein the abrasive body has an abrasive layer formed of a plurality of bonding layers, with at least an inner bonding layer, an outer bonding layer and abrasive grains,
wherein the inner bonding layer holds the abrasive grains in the abrasive layer, and wherein the outer bonding layer covers the abrasive grains, and
wherein a binding agent of the outer bonding layer is a transparent or translucent binding agent and wherein thermochromic colouring agents are mixed into the inner bonding layer.

5. The grinding tool according to claim 4, wherein the binding agent of the outer bonding layer is the same binding agent of the inner bonding layer.

6. The grinding tool according to claim 4 wherein a binding agent of the inner bonding layer and the binding agent of the outer bonding layer are different binding agents.

7. The grinding tool according to claim 4, wherein the transparent or translucent binding agent of the outer bonding layer is a thermosetting plastic.

8. The grinding tool according to claim 4, wherein the binding agent of the inner bonding layer is an organic or an inorganic binding agent.

9. The grinding tool according to claim 4, wherein the abrasive body has a substrate layer.

10. The grinding tool according to claim 9, wherein a non-thermochromic colour is applied on an upper face of the substrate layer facing to the abrasive layer.

11. The grinding tool according to claim 4, wherein at least one partial amount of the abrasive grains is formed transparent.

12. The grinding tool according to claim 4, wherein at least a partial amount of the abrasive grains is formed coloured.

13. The grinding tool according to claim 4, wherein the abrasive grains have a grain size between 30 and 1400 micrometers.

14. The grinding tool according to claim 4, wherein the thermochromic colouring agents comprise reversible and/or irreversible thermochromic colouring agents.

15. The grinding tool according to claim 4, wherein the thermochromic colouring agents have at least one colour change temperature such, that their colour changes at least once between 40 degrees Celsius and 60 degrees Celsius.

16. The grinding tool according to claim 4, wherein the thermochromic colouring agents are formed such, that at least one colour change of the thermochromic colouring agents takes place continuously or discontinuously.

17. The grinding tool according to claim 4, wherein the thermochromic colouring agents are formed such, that these turn transparent at least at one colour change temperature.

18. The grinding tool according to claim 4, wherein the thermochromic colouring agents are formed such, that a colour change takes place at a first colour change temperature and a further colour change takes place at a second colour change temperature.

19. The grinding tool according to claim 18, wherein the colour change is reversible at the first colour change temperature and the colour change is irreversible at the second colour change temperature.

20. The grinding tool according to claim 19, wherein the second colour change temperature is higher than the first colour change temperature.

* * * * *